United States Patent

Shroot et al.

[11] Patent Number: 4,874,747
[45] Date of Patent: Oct. 17, 1989

[54] POLYCYCLIC HETEROCYCLIC COMPOUNDS, A PROCESS FOR THEIR PREPARATION AND THEIR USE IN HUMAN AND VETERINARY MEDICINE

[75] Inventors: Braham Shroot, Antibes; Jacques Eustache, Grasse; Jean-Michel Bernardon, Nice; Philippe Nedoncelle, Grasse, all of France

[73] Assignee: Centre International de Recherches Dermatologiques (CIRD), Valbonne, France

[21] Appl. No.: 188,547

[22] Filed: Apr. 29, 1988

[30] Foreign Application Priority Data

Apr. 30, 1987 [FR] France ................. 87 06152

[51] Int. Cl.$^4$ ............... A61K 31/42; A61K 31/535; C07D 413/10
[52] U.S. Cl. ............................. 514/23; 536/18.7; 544/137; 544/368; 546/198; 548/224; 514/232.8; 514/253; 514/321; 514/375; 514/863; 514/880; 514/912
[58] Field of Search ............... 514/232.8, 253, 321, 514/375, 23; 544/137, 368; 546/198; 536/18.7; 548/224

[56] References Cited

U.S. PATENT DOCUMENTS 4,659,360 4/1987 Baum et al. ............... 548/224
4,740,519 4/1988 Shroot et al. ............. 514/443

FOREIGN PATENT DOCUMENTS 1156800 7/1969 United Kingdom ............. 548/224

Primary Examiner—Mary C. Lee
Assistant Examiner—Mary Sue Howard
Attorney, Agent, or Firm—Cushman, Darby & Cushman

[57] ABSTRACT

A polycyclic heterocyclic compound has the formula

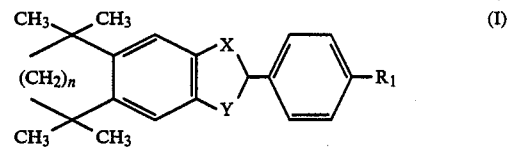

wherein
n is 1 or 2,
$R_1$ represents (i) lower alkyl, (ii) —$CH_2$ OH or (iii)

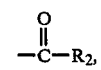

$R_2$ represents (a) hydrogen, (b)

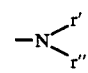

or (c)—$OR_3$,
$R_3$ represents hydrogen, $C_1$–$C_{20}$ alkyl mono or polyhydroxyalkyl, aryl or aralkyl optionally substituted, the residue of a sugar or

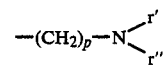

wherein p is 1, 2, or 3, and r' and r'' represent hydrogen, lower alkyl, mono or polyhydroxyalkyl, aryl optionally substituted, amino acid residue, aminated sugar residue, or together form a heterocycle,
X represents oxygen, sulfur, SO, $SO_2$ or —$NR_4$,
Y represents $CR_4$ or a nitrogen atom and
$R_4$ represents hydrogen or lower alkyl.

This polycyclic heterocyclic compound can be used in human and veterinary medicine and especially in the topical or systemic treatment of determatologic diseases.

12 Claims, No Drawings

POLYCYCLIC HETEROCYCLIC COMPOUNDS, A PROCESS FOR THEIR PREPARATION AND THEIR USE IN HUMAN AND VETERINARY MEDICINE

BACKGROUND OF THE INVENTION

The present invention relates to polycyclic heterocyclic derivatives, to processes for their preparation and their use in human and veterinary medicine and in cosmetic compositions.

These heterocyclic derivatives find use in the topical and systemic treatment of dermatologic diseases linked to a keratinization disorder (differentiation-proliferation) and dermatologic disorders, or others, having inflammatory and/or immunoallergic components and in the treatment of conjunctive tissue degeneration illnesses. These derivatives also exhibit antitumoral activity. Moreover, these derivatives can be employed in the treatment of atrophy, be it cutaneous or respiratory and in the treatment of rheumatoid psoriasis.

Lastly, they find use in the ophthalmologic field, principally in the treatment of corneopathies.

The polycyclic heterocyclic derivatives in accordance with the present invention can be represented by the formula wherein n is 1 or 2, $R_1$ represents (i) lower alkyl, (ii) —CH$_2$OH or (iii)

$$-\overset{O}{\underset{\|}{C}}-R_2,$$

$R_2$ represents (a) hydrogen, (b)

$$-N\overset{r'}{\underset{r''}{\diagdown}}$$

or (c) —OR$_3$ wherein $R_3$ represents hydrogen, alkyl having 1-20 carbon atoms, mono or polyhydroxyalkyl, aryl or aralkyl optionally substituted or the residue of a sugar or $$-(CH_2)_p-N\overset{r'}{\underset{r''}{\diagdown}}$$

wherein p is 1, 2 or 3, r' and r" represent hydrogen, lower alkyl, monohydroxyalkyl, polyhydroxyalkyl, aryl optionally substituted, amino acid residue, aminated sugar residue or, taken together, form a heterocycle, X represents oxygen, sulfur, SO, SO$_2$ or —NR$_4$, Y represents CR$_4$ or a nitrogen atom, and R$_4$ represents hydrogen or lower alkyl, and the salts of said polycyclic heterocyclic derivatives of formula I.

By alkyl having 1-20 carbon atoms is meant, principally, methyl, ethyl, propyl, 2-ethylhexyl, octyl, dodecyl, hexadecyl and octadecyl.

By lower alkyl is meant a radical having 1-4 carbon atoms and principally methyl, ethyl, isopropyl, butyl and tert.butyl.

By monohydroxyalkyl is meant a radical having 2-4 carbon atoms and principally 2-hydroxyethyl, 2-hydroxypropyl and 2'-hydroxy-2-ethoxy ethyl.

By polyhydroxyalkyl is meant a radical containing 3-6 carbon atoms and 2-5 hydroxyl groups such as 2,3-dihydroxypropyl, 2,3,4-trihydroxybutyl, 2,3,4,5-tetrahydroxypentyl or the residue of pentaerythritol.

By residue of a sugar is meant a residue derived, for example, from glucose, mannose, erythrose or galactose.

Representative aminated sugar residues include those derived from glucosamine, galactosamine or mannosamine.

By aryl is meant phenyl optionally substituted by halogen, hydroxy, a nitro function or lower alkyl.

Representative preferred aralkyls include, preferably, benzyl as well as phenethyl.

When r' and r" taken together form a heterocycle, the heterocycle can be piperidino, piperazino, morpholino, pyrrolidino or 4-(2'-hydroxyethyl) piperazino.

When the compounds of the present invention are provided in the form of salts they can be salts of an alkali or alkaline earth metal or even of zinc, or of an organic amine when they have at least one free acid function, or salts of a mineral or organic acid, principally, hydrochlorides, hydrobromides or citrates when they have at least one amine function.

Representative compounds of formula I include, principally, the following:

methyl ester of p-(5,6,7,8-tetrahydro-5,5,8,8-tetramethyl-2-naphtho[2,3-b]furyl) benzoic acid, p-(5,6,7,8-tetrahydro-5,5,8,8-tetramethyl-2-naphtho[2,3-b]furyl) benzoic acid, methyl ester of p-(5,6,7,8-tetrahydro-5,5,8,8-tetramethyl-2-naphtho[2,3-b]thienyl) benzoic acid, p-(5,6,7,8-tetrahydro-5,5,8,8-tetramethyl-2-naphtho[2,3-b]thienyl) benzoic acid, p-(5,6,7,8-tetrahydro-5,5,8,8-tetramethyl-2-1H-benz[f]indolyl) benzoic acid, methyl ester of p-(5,6,7,8-tetrahydro-5,5,8,8-tetramethyl-2-1H-benz[f]indolyl) benzoic acid, methyl ester of p-(1-methyl-5,6,7,8-tetrahydro-5,5,8,8-tetramethyl-2-benz[f]indolyl) benzoic acid, p-(1-methyl-5,6,7,8-tetrahydro-5,5,8,8-tetramethyl-2-benz[f]indolyl) benzoic acid, methyl ester of p-(5,6,7,8-tetrahydro-5,5,8,8-tetramethyl-2-naphth[2,3-d]oxazolyl) benzoic acid, p-(5,6,7,8-tetrahydro-5,5,8,8-tetramethyl-2-naphth[2,3-d]oxazolyl) benzoic acid, p-(5,6,7,8-tetrahydro-5,5,8,8-tetramethyl-2-naphth[2,3-d]oxazolyl) benzyl alcohol, p-(5,6,7,8-tetrahydro-5,5,8,8-tetramethyl-2-naphth[2,3-d]oxazolyl) benzoic aldehyde, ethylamide of p-(5,6,7,8-tetrahydro-5,5,8,8-tetramethyl-2-naphth[2,3-d]oxazolyl) benzoic morpholide of p-(5,6,7,8-tetrahydro-5,5,8,8-tetramethyl-2-naphth[2,3-d]oxazolyl) benzoic acid, 2-hydroxyethyl ester of p-(5,6,7,8-tetrahydro-5,5,8,8-tetramethyl-2-naphth[2,3-d]oxazolyl) benzoic acid, methyl ester of p-(5,6,7,8-tetrahydro-5,5,8,8-tetramethyl-2-naphth[2,3-d]imidazolyl) benzoic acid, p-(5,6,7,8-tetrahydro-5,5,8,8-tetramethyl-2-naphth[2,3-d]imidazolyl) benzoic acid and
2-(4-methyl)phenyl-5,6,7,8-tetrahydro-5,5,8,8-tetramethyl-naphth[2,3-d]imidazole.

Particularly preferred compounds of formula I in accordance with the present invention are those having the following formula:

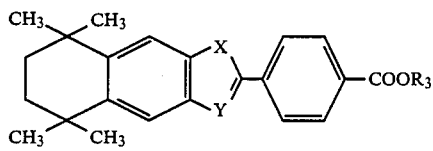

wherein
$R_3$ represents hydrogen or lower alkyl,
X represents oxygen, sulfur or $NR_4$,
Y represents $CR_4$ or a nitrogen atom, and
$R_4$ represents hydrogen or methyl.

Representative compounds corresponding to formula II include, principally:
p-(5,6,7,8-tetrahydro-5,5,8,8-tetramethyl-2-naphtho[2,3-b]thienyl) benzoic acid and its methyl ester,
p-(5,6,7,8-tetrahydro-5,5,8,8-tetramethyl-1H-benz[f]indolyl) benzoic acid and its methyl ester,
p-(5,6,7,8-tetrahydro-5,5,8,8-tetramethyl-2-naphth[2,3-d]oxazolyl) benzoic acid and its methyl ester,
p-(5,6,7,8-tetrahydro-5,5,8,8-tetramethyl-2-naphth[2,3-d]imidazolyl)benzoic acid and its methyl ester, and
p-(1-methyl-5,6,7,8-tetrahydro-5,5,8,8-tetramethyl-2-benz[f]indolyl) benzoic acid and its methyl ester.

The present invention also relates to a process for the preparation of the compounds of formula I.

These compounds can be obtained in accordance with two synthesis methods:

(A) The First method (Scheme I)

This method is particularly preferred when, in the compounds of formula I, Y represents a nitrogen atom.

This method comprises reacting an aromatic carboxylic acid derivative of formula (1) with an aromatic diamino, hydroxyamino or thioamino derivative of formula (2).

Scheme I

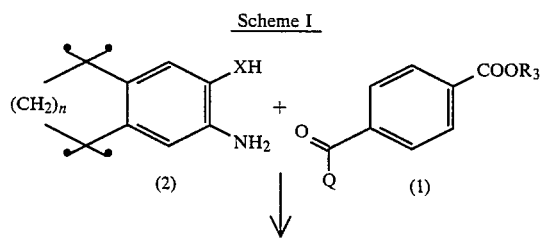

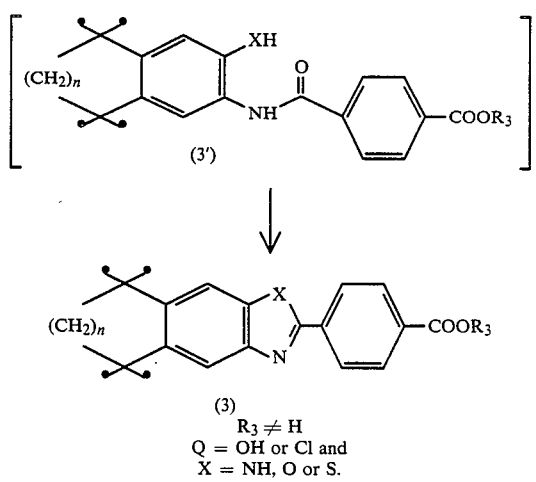

$R_3 \neq H$
Q = OH or Cl and
X = NH, O or S.

The action of the acid chloride (1) (Q=Cl) on the aromatic amino compound (2) leads to the intermediate (3') which is isolated. In the same way, the coupling of the acid (1) (Q=OH) with the compound (2), in the presence of triphenylphosphine and dicyclohexylcarbodiimide, or diethylazodicarboxylate and triphenylphosphine, in a known manner, leads to intermediate compounds (3').

This intermediate compound (3') is then cyclized by acid treatment to give compounds of formula (3). There can be employed for this cyclization reaction a sulfonic acid such as p-toluene sulfonic acid in an inert solvent such as toluene or xylene. The cyclization reaction temperature is preferably close to the reflux temperature of the solvent employed.

In accordance with a variation of this process, it is possible to directly produce the compounds of formula (3) by direct heating of the acid of formula (1) (Q=OH) and the aromatic amino compound (2) in an inert solvent such as xylene in the presence of an acid catalyst; for example, p-toluene sulfonic acid at the reflux temperature of the solvent.

(B) Second method (Scheme II)

The method is quite particularly preferred when, in the compounds of formula I, Y represents $CR_4$.

Scheme II

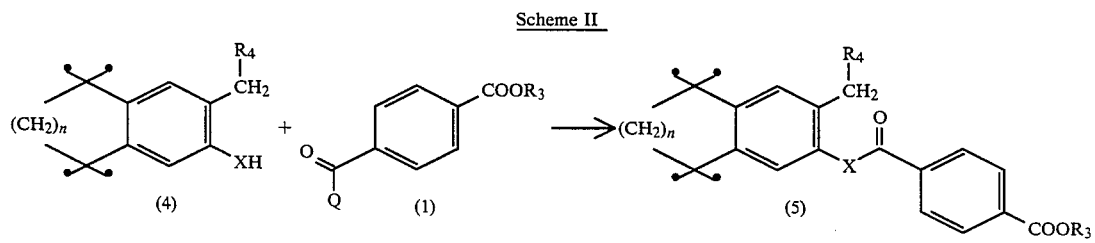

-continued
Scheme II

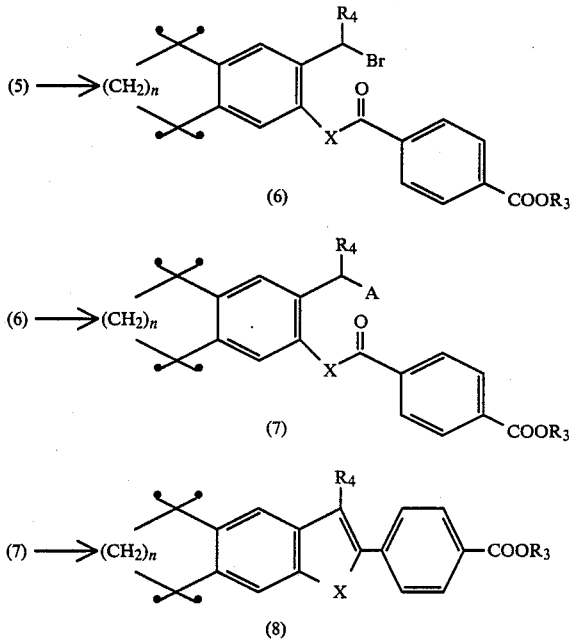

$R_3 = H$
$Q = OH$ or $Cl$,
$X = NH$, $O$ or $S$, $A = -\overset{+}{P}(V)_3Br^-$ wherein V is alkyl or aryl or $-\underset{\underset{O}{\|}}{P}-(W)_2$ wherein W is aryl, alkoxy or aryloxy.

In accordance with this second method, the cyclization reaction, that is, the conversion of the derivative (7) having a phosphonium or phosphinyl group to compound (8) is effected in accordance with the Wittig or Wittig-Horner reaction conditions, that is, in the presence of a base which can be a hydroxide or carbonate of an alkali metal, for example, lithium hydroxide or potassium carbonate, an alkali metal hydride, for example, sodium hydride, an alkali metal alcoholate, for example, sodium methylate or potassium tert.butoxide, a tertiary amine, for example, triethylamine, di-isopropylethylamine or diazabicycloundecene (DBU) or even an alkali amide, for example, sodium amide or lithium di-isopropylamide. The reaction temperature is between $-78°$ C. and $+150°$ C. and there can be employed, as a solvent, a dipolar aprotic solvent (dimethylsulfoxide or dimethylformamide), an alcohol, or an ether (dioxane or tetrahydrofuran). The reaction is advantageously carried out in tetrahydrofuran (THF) at a temperature between 0° C. and 80° C. using triethylamine or DBU as the base.

The bromination reaction, i.e., the production of the compound of formula (6) is carried out in the presence of N-bromosuccinimide in previously dried benzene or carbon tetrachloride, the temperature preferably being between 70° C. and 90° C., the radical initiator being, preferably, benzoyl peroxide.

The acylation reaction, i.e., the production of the compound of formula (5) is carried out in a conventional manner. When X represents NH, the reaction is advantageously effected using the compound of formula (1) in the form of an acid chloride (Q=Cl) in the presence of a tertiary amine.

The compounds produced in accordance with the two methods described above can be converted in accordance with conventional procedures to provide compounds having any of the other meanings of $R_1$ set forth above.

Thus, saponification of esters gives the corresponding acids which can then be transformed into acid chlorides which are then easily converted into amides. These amides can also be obtained by the direct reaction of amines with previously obtained esters. Reduction of esters, aldehyde or amide by an appropriate reducing agent (for example, lithium aluminum hydride) produces corresponding alcohols and amines.

The present invention also relates to, as novel industrial products, synthesis intermediates having the formula

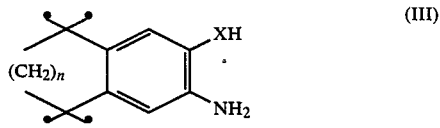

(III)

wherein
n is 1 or 2,
X represents oxygen, sulfur or $NR_4$, and
$R_4$ represents hydrogen or lower alkyl.
Representative intermediate compounds of formula III include particularly the following:
2,3-diamino-5,6,7,8-tetrahydro-5,5,8,8-tetramethyl naphthalene and 3-amino-5,6,7,8-tetrahydro-5,5,8,8-tetramethyl-2-naphthol.

The compounds of the present invention exhibit excellent activity in the inhibition test of ornithine decarboxylase in nude rats, after induction, by "tape stripping," M. Bouclier et al., Dermatologica, 169, No. 4, 1984. This test is recognized as a measure of the activity of retinoides on cellular proliferation phenomena.

These compounds are particularly appropriate for treating dermatologic ailments linked to a keratinization disorder (differentiation-proliferation) as well as dermatologic diseases having an inflammatory and/or immunoallergic component, principally:

acne vulgaris, comedons or polymorphs, solar senile acne and medicinal or professional acne,
solar keratites,
extensive or severe forms of psoriasis, and other keratinization disorders and principally ichtysoses and ichtysosis like conditions,
Darier malady,
palmo-plantar keratodermies,
leucophasies and leucophasis-like states, lichen plan, and
all malignant or benign dermatologic proliferations, severe or extensive.

They are also active for certain rheumatoid disorders, in the treatment of tumors, of rheumatoid psoriasis, cutaneous or respiratory atrophies as well as in certain ophthalmologic problems relating to corneopathies.

These compounds can also be employed to combat against ageing of the skin and in particular ageing due to the effects of the sun.

Thus the present invention also relates to medicinal compositions containing at least one compound of formula I, such as defined above, or one of its salts.

The present invention thus relates to a new medicinal composition, intended principally for the treatment of the above-mentioned disorders, comprising in a pharmaceutically acceptable support, an effective amount of at least one compound of formula I or one of its salts.

The compounds according to the present invention are generally administered at a daily dosage of about 0.01μg/kg to 1 mg/kg of body weight.

As the vehicle or carrier for these compositions any conventional vehicle can be employed, the active component being found either in the dissolved state, or in the dispersed state, in said vehicle.

The administration of the compounds of the present invention can be effected enterally, parenterally, rectally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered rectally, the compositions can be provided in the form of suppositories.

When administered topically, the pharmaceutical compositions, based on the compounds according to the present invention, can be provided in the form of ointments, tinctures, creams, salves, powders, pads, impregnated tampons, solutions, lotions, gels, sprays or suspensions. The compositions for topical administeration contain preferably from 0.00001 to about 0.01 percent by weight of the compound of formula I. These compositions for topical administration can be provided under anhydrous form or in aqueous form according to clinical indications.

When administered ocularly, the composition is provided principally in the form of an eyewash.

The compounds of formula I, according to the present invention, are also useful in the cosmetic field, and n particular in body and hair hygiene compositions and principally for the treatment of skin having acne tendencies, to improve the growth of hair, i.e., to promote the growth of existing hair follicles, to combat hair loss, to combat against an oily appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula I or one of its salts, this composition being provided principally in the form of a lotion, gel, soap or shampoo.

The concentration of the compound of formula I in these cosmetic compositions is between 0.00001 and 0.01 percent by weight based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, S-benzylcysteamine, their salts and their derivatives, tioxolone or benzoyl peroxide; antibiotics such as erythromycin and its esters, neomycin, tetracyclines or 4-polymethylene-4-isothiazoline-3-ones; agents promoting the growth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidine dione); steroidal and non-steroidal anti-inflammatory agents; carotenoids and, principally, β-carotene; anti-psoriasic agents such as anthralin and its derivatives and 5,8,11,14-eicosatetraynoic and 5,8,11-eicosatriynoic acids, and their esters and amides.

The compositions according to the present invention can also include flavor improving agents, preservatives, stabilizers, humidity regulating agents, pH regulating agents, osmotic pressure modifying agents, emulsifiers, anti-oxidants such as α-tocopherol, butylhydroxyanisole or butylhydroxytoluene.

The following non-limiting examples illustrate the preparation of the active compounds of formula I according to the present invention as well as compositions containing these compounds.

Examples of Preparation

EXAMPLE 1

Preparation of the methyl ester of p-(5,6,7,8-tetrahydro-5,5,8,8-tetramethyl-2-naphtho[2,3-b]furanyl) benzoic acid (a) 3-methyl-5,6,7,8-tetrahydro-5,5,8,8p-(5,6,7,8-tetramethyl-2-naphthol Into a round bottom flask there are introduced 10.8 g (100 mmoles) of ortho cresol, 100 ml of dichloromethane ($CH_2Cl_2$) and 18.3 g (100 mmoles) of 2,4-dichloro-2,4-dimethylhexane. The reaction mixture is cooled to 5° C. and there are added, in small quantities, 6.6 g (50 mmoles) of aluminum chloride. The temperature is permitted to rise to 20° C. The reaction mixture is stirred for 2 hours and it is then poured into 200 ml of water. The organic phase is decanted, dried on magnesium sulfate (MgSO$_4$) and the solvents are evaporated. The residue is recrystallized in 100 ml of hexane, yielding 20.3 g (93%) of 3-methyl-5,6,7,8-tetrahydro-5,5,8,8-tetramethyl-2-naphthol which melts at 122–123° C.

(b) methyl ester of p-(3-methyl-5,6,7,8-tetrahydro-5,5,8,8-tetramethyl-2-naphthyloxy carbonyl) benzoic acid In 100 ml of tetrahydrofuran (THF) there are dissolved 8.7 g (40 mmoles) of the naphthol obtained in 1(a) above and 6.2 ml (44 mmoles) of triethylamine. A solution of p-(methoxycarbonyl) benzoyl chloride (8.8 g=44 mmoles) in THF (50 ml) is slowly added and the reaction mixture is stirred for 4 hours at ambient temperature. The reaction mixture is poured into 200 ml of water and extracted with 300 ml of CH$_2$Cl$_2$. The organic phase is decanted, dried on MgSO$_4$ and the solvents are evaporated. The residue is recrystallized in isooctane, yielding 11 g (72%) of the methyl ester of p-(3-methyl-5,6,7,8-tetrahydro-5,5,8,8-tetramethyl-2-naphthyloxy carbonyl) benzoic acid which melts at 111–112° C.

(c) Methyl ester of p-(3-bromomethyl-5,6,7,8-tetrahydro-5,5,8,8-tetramethyl-2-naphthyloxy carbonyl) benzoic acid A mixture of the ester obtained in 1(b) (10.60 g; 27.8 mmoles), benzoyl peroxide (50mg) and carbon tetrachloride (CCl$_4$), (150 ml) is brought to reflux. There are then added, in small quantities, 4.96 g (27.8 mmoles) of N-bromosuccinimide (NBS).

Reflux is maintained for 24 hours and the solvent is evaporated. The residue is purified by passage through a silica column (eluant: 1/1 mixture of hexane/CH$_2$Cl$_2$). 12 g of a mixture containing 80% of the expected ester and 20% of the starting ester are recovered.

(d) Methyl ester of p-(5,6,7,8-tetrahydro-5,5,8,8-tetramethyl-naphtho[2,3-b]furanyl-2-yl) benzoic acid In a round bottom flask, 11.8 g of the mixture obtained in 1(c), 100 ml of THF and 6.50 g (24.6 mmoles) of triphenylphosphine are introduced. The reaction mixture is heated at reflux for 4 hours and cooled to 10° C. There are then slowly added 3.70 ml (24.6 mmoles) of 1,8-diazabicyclo (5.4.0) undec-7-ene (DBU). The reaction mixture is permitted to return to ambient temperature and it is stirred for 5 hours. The reaction mixture is then poured into water, extracted with ether, dried on MgSO$_4$ and the solvents are evaporated.

The residue is purified by passage through a silica column (eluant: 1/1 mixture of hexane/CH$_2$Cl$_2$). 4.20 g of the methyl ester of p-(5,6,7,8-tetrahydro-5,5,8,8-tetramethyl-2-naphtho[2,3,b]furanyl) benzoic acid which melts at 184–185° C. are recovered.

EXAMPLE 2

Preparation of p-(5,6,7,8-tetrahydro-5,5,8,8-tetramethyl-2-naphtho[2,3,b]furanyl) benzoic acid 3.80 g (10.4 mmoles) of the ester obtained in 1(d) above are treated at reflux for 4 hours with 200 ml of 2N methanolic soda. The methanol is evaporated and the remainder is taken up in water and acidified with concentrated HCl. The reaction mixture is extracted with ether and the organic phase is decanted, dried on MgSO$_4$ and the solvents are evaporated. The residue is recrystallized in a 2/1 mixture of diisopropyl ether and ethyl acetate. 3.50 g (97%) of p-(5,6,7,8-tetrahydro-5,5,8,8-tetramethyl-2-naphtho[2,3,b]furanyl) benzoic acid which melts at 307–312° C. are recovered.

EXAMPLE 3

Methyl ester of p-(5,6,7,8-tetrahydro-5,5,8,8-tetramethyl-2-naphtho[2,3-b]thienyl) benzoic acid (a) 2-(N,N-dimethylthiocarbamoyloxy)-3-methyl-5,6,7,8-tetrahydro-5,5,8,8-tetramethyl naphthalene In a round bottom flask there are introduced 1.7 g (57 mmoles) of sodium hydride (80% in oil) and 50 ml of dimethylformamide. There is slowly added a solution of 10.3 g (47 mmoles) of 3-methyl-5,6,7,8-tetrahydro-5,5,8,8-tetramethyl-2-naphthol in 100 ml of DMF and the reaction mixture is stirred until the cessation of gas evolvement. There are then added 8.1 g (66 mmoles) of dimethylthio-carbamoylchloride in 100 ml of DMF and the reaction mixture is stirred for 4 hours at ambient temperature. The reaction mixture is poured into water and extracted with ethylether. The organic phase is decanted, washed with water, dried on MgSO$_4$ and the solvent evaporated. The residue is purified by chromatography on a silica column (eluant: 20/80 mixture of CH$_2$Cl$_2$/hexane). 13.2 g (92%) of 2-(N,N-dimethylthiocarbamoyloxy)-3-methyl-5,6,7,8-tetrahydro-5,5,8,8-tetramethyl naphthalene which melts at 102–103° C. are recovered.

(b) 2-N,N-dimethylcarbamoylthio)-3-methyl-5,6,7,8-tetrahydro-5,5,8,8-tetramethyl naphthalene 13 g (42.5 mmoles) of the compound obtained in 3(a) above are heated under nitrogen at 280° C. After cooling, the residue is passed through a silica column (eluant: 70/30 mixture of hexane/CH$_2$Cl$_2$).

10.2 g (79%) of 2-(N,N-dimethylcarbamoylthio-3-methyl-5,6,7,8-tetahydro-5,5,8,8-tetramethyl naphthalene which melts at 142–143° C. are obtained.

(c) 3-methyl-5,6,7,8-tetrahydro-5,5,8,8-tetramethyl-2-thionaphthol 9.2 g (30 mmoles) of the product obtained in 3(b) above are treated at reflux with 200 ml of 2N methanolic soda for 2 hours. The solvents are evaporated and the remainder is taken up in water, acidified to pH 0 (concentrated HCl) and extracted with ether. The organic phase is decanted, dried on magnesium sulfate and the solvents are evaporated. 6.9 g (98%) of 3-methyl-5,6,7,8-tetrahydro-5,5,8,8-tetramethyl-2-thionaphthol which melts at 91–92° C. are obtained.

(d) Methyl ester of p-(3-methyl-5,6,7,8-tetrahydro-5,5,8,8-tetramethyl-2-naphthylthio) carbonyl benzoic acid In a round bottom flask there are introduced 5.9 g (33 mmoles) of the monomethyl ester of terephthalic acid and 50 ml of THF. There are then added, by small portions, 5.3 g (33 mmoles) of 1,1'-carbonyldiimidazole. The reaction mixture is stirred until the cessation of gaseous emissions. There are then added 7 g (30 mmoles) of the compound obtained in 3(c) above in 50 ml of THF and the mixture is stirred for 7 hours at ambient temperature.

The reaction mixture is poured into water, extracted with ether and washed with a saturated solution of sodium bicarbonate. The organic phase is decanted, dried on MgSO4 and the solvent evaporated. The residue is recrystallized in isooctane to give 9.5 g (81%) of the methyl ester of p-(3-methyl-5,6,7,8-tetrahydro-5,5,8,8-tetramethyl-2-naphthylthio) carbonyl benzoic acid which melts at 105–106° C.

(e) Methyl ester of p-(3-bromomethyl-5,6,7,8-tetrahydro-5,5,8,8-tetramethyl-2-naphthylthio) carbonyl benzoic acid 9.26 g (23 mmoles) of the compound prepared in 3(d) above are heated at reflux in 150 ml of carbon tetrachloride containing 50 mg of benzoyl peroxide. There are then added, in small amounts, 4.16 g (23 mmoles) of N-bromosuccinimide and once the addition has ended, reflux is maintained for 12 hours. The solvent is evaporated and the residue is purified by chromatography on a silica column (eluant: 1/1 mixture of $CH_2Cl_2$/hexane). 10.8 g of a mixture of the expected monobromo derivative (85%) and nonbrominated and dibrominated (15%) are obtained. (Dosage effected by comparing the integration of signals in NMR of the proton of the methyl, bromomethyl and dibromomethyl groups in the compounds of the mixture). The mixture is used as such for the following synthesis.

(f) Methyl ester of p-(5,6,7,8-tetrahydro-5,5,8,8-tetramethyl-2-naphtho[2,3-b]thienyl) benzoic acid In a round bottom flask, there are introduced 10.5 g of the preceding mixture, 6 g (23 mmoles) of triphenylphosphine and 100 ml of THF. The reaction mixture is heated at reflux for 4 hours and cooled to 10° C. 3.5 ml (23 mmoles) of DBU are added and the reaction mixture is stirred for 4 hours at ambient temperature, poured into water and extracted with ether. The organic phase is decanted, dried on MgSO4 and the solvent evaporated. The residue is purified by chromatograph on a silica column (eluant: 80/20 mixture of hexane/dichloromethane). 6.6 g of the methyl ester of p-(5,6,7,8-tetrahydro-5,5,8,8-tetramethyl-2-naphtho[2,3-b]thienyl) benzoic acid which melts at 186–187° C. are obtained.

EXAMPLE 4

Preparation of p-(5,6,7,8-tetrahydro-5,5,8,8-tetramethyl-2-naphtho[2,3-b]thienyl) benzoic acid 5 g (13 mmoles) of the ester obtained in 3(f) are treated with 200 ml of 2N methanolic soda. The reaction mixture is heated at reflux for 2 hours, evaporated to dryness, taken up in water, acidified to pH=1 with concentrated HCl and extracted with ether. The organic phase is decanted, dried on MgSO4 and the solvent evaporated. The residue is recrystallized in a 2/1 mixture of isopropylether/ethyl acetate. 4.6 g (96%) of p-(5,6,7,8-tetrahydro-5,5,8,8-tetramethyl-2-naphtho[2,3-b]thienyl) benzoic acid which melts at 291–292° C. are obtained.

EXAMPLE 5

Preparation of p-(5,6,7,8-tetrahydro-5,5,8,8-tetramethyl-2-1H-benz[f]indolyl) benzoic acid (a) 2-methyl-5,6,7,8-tetrahydro-5,5,8,8-tetramethyl naphthalene In a round bottom flask there are introduced 64 ml (600 mmoles) of toluene and 36.6 g (200 mmoles) of 2,5-dichloro-2,5-dimethyl hexane. The reaction mixture is cooled to 0° C. and there are added, by small amounts, 4.1 g (30 mmoles) of aluminum chloride. The reaction mixture is stirred for 1 hour at ambient temperature, poured into water and extracted with $CH_2Cl_2$. The organic phase is decanted, dried on magnesium sulfate and evaporated. The resulting oil is purified by distillation. 39.4 g (98%) of 2-methyl-5,6,7,8-tetrahydro-5,5,8,8-tetramethyl naphthalene which boils at 68° C. (under 1 mm of mercury) are obtained.

(b) 2-methyl-3-nitro-5,6,7,8-tetrahydro-5,5,8,8-tetramethyl naphthalene 50 g (250 mmoles) of 2-methyl-5,6,7,8-tetrahydro-5,5,8,8-tetramethyl naphthalene are dissolved in 200 ml of acetic anhydride. The solution is cooled to 0° C. and there is slowly added a solution of 10.5 ml (250 mmoles) of nitric acid, 20 ml of acetic acid and 20 ml of acetic andydride, while maintaining the temperature between 0 and 5° C. The reaction mixture is then stirred for 1 hour at ambient temperature, poured into ice water and filtered. The resulting solid is washed with water. The solid is dissolved in methylene chloride, washed with water and then with a saturated solution of sodium bicarbonate, dried on MgSO4 and evaporated. 45.8 g (74%) of 2-methyl-3-nitro-5,6,7,8-tetrahydro-5,5,8,8-tetramethyl naphthalene which melts at 143–144° C. are obtained.

(c) 3-methyl-5,6,7,8-tetrahydro-5,5,8,8-tetramethyl-2-naphthylamine 24.7 g (100 mmoles) of the nitro derivative obtained in 5(b) are dissolved in 400 ml of ethanol. To this solution there are added 33.6 g (600 mmoles) of powdered iron and then, slowly, 38 ml of concentrated HCl. The reaction mixture is heated at reflux for 1 hour and evaporated to dryness. The residue is taken up in water to which is added with caution an excess of sodium bicarbonate. The mixture is then extracted with ether, filtered and the filtrate is recovered, dried on MgSO4 and evaporated. 21.2 g (98%) of 3-methyl-5,6,7,8-tetrahydro-5,5,8,8-tetramethyl-2-naphthylamine which melts at 94–95° C. are obtained.

(d) Methyl ester of p-[(3-methyl-5,6,7,8-tetrahydro-5,5,8,8-tetramethyl-2-naphthyl)carbamoyl] benzoic acid 8.1 g (45 mmoles) of methyl monoterephthalate are dissolved in 100 ml of THF. To this solution there are added, by small quantities, 8 g (45 mmoles) of 1,1'-carbonyldiimidazole. The mixture is stirred until the gaseous emissions have ceased and then there is slowly added a solution of 9.8 g (45 mmoles) of the amine obtained in 5(c) above in 50 ml of THF. The reaction mixture is stirred for 2 hours at ambient temperature, poured into water and extracted with $CH_2Cl_2$. The organic phase is decanted, dried on $MgSO_4$ and evaporated.

The residue is recrystallized in isopropylether to give 14.6 g (86%) of the methyl ester of p-[(3-methyl-5,6,7,8-tetrahydro-5,5,8,8-tetramethyl-2-naphthyl)carbamoyl] benzoic acid which melts at 169-170° C.

(e) Methyl ester of p-[(N-tert.butoxycarbonyl-3-methyl-5,6,7,8-tetrahydro-5,5,8,8-tetramethyl-2-naphthylcarbamoyl)] benzoic acid In a round bottom flask there are introduced 1.2 g (40.5 mmoles) of sodium hydride (80% in oil), 20 ml of DMF and 30 ml of THF. There is slowly added a solution of 13.9 g (37 mmoles) of the ester obtained in 5(d) in 60 ml of THF. The reaction mixture is stirred until the gaseous emissions have ceased. There are then added 8.8 g (40.5 mmoles) of di-tert.butyl dicarbonate in 100 ml of THF and the mixture is stirred at ambient temperature for 4 hours. The reaction mixture is poured into water and extracted with ethyl ether. The organic phase is decanted, washed with water, dried on $MgSO_4$ and evaporated. The residue is purified by chromatography on a silica column (eluant: 7/3 mixture of dichloromethane/hexane). 14.1 g (82%) of the methyl ester of p-[(N-tert.butoxy carbonyl-3-methyl-5,6,7,8-tetrahydro-5,5,8,8-tetramethyl-2 -naphthylcarbamoyl)] benzoic acid which melts at 176-177° C. are obtained.

(f) Methyl ester of p-(3-bromomethyl-N-tert.butoxycarbonyl-5,6,7,8-tetrahydro-5,5,8,8-tetramethyl-2-naphthylcarbamoyl) benzoic acid 13.25 g (27.6 mmoles) of the ester obtained in 5(e) are placed in a round bottom flask. There are added 150 ml of carbon tetrachloride and 50 mg of benzoyl peroxide The mixture is heated at reflux and there are introduced, in small amounts, 4.9 g (27.6 mmoles) of N-bromosuccinimide. Reflux is maintained for 12 hours. The solvent is evaporated and the residue is purified by chromatography on silica, by eluting with a 1/1 mixture of dichloromethane and hexane. 14.2 g are obtained of a mixture containing about 85% of the expected monobromo derivative and 15% of a mixture of dibromonated product and starting product (these proportions being estimated by NMR, in a manner analogous to that of Example 3(e). The mixture is used as such in the following synthesis.

(g) Methyl ester of p-(N-tert.butoxycarbonyl-5,6,7,8-tetrahydro-5,5,8,8-tetramethyl-2-1H-benz[f] indolyl) benzoic acid Into a round bottom flask there are introduced 13.9 g of the mixture obtained in 5(f), 6.7 g (25.5 mmoles) of triphenyl phosphine and 100 ml of THF. The mixture is heated at reflux for 8 hours and then cooled to 5° C. There are then slowly added 3.8 ml (25.5 mmoles) of DBU. The reaction mixture is stirred at ambient temperature for 2 hours, poured into water and extracted with ether. The organic phase is decanted, dried on $MgSO_4$ and evaporated. The residue is purified by chromatography on a silica column (eluant: 20/80 mixture of $CH_2Cl_2$/hexane). 6.7 g (69%) of the methyl ester of p-(N-tert.butoxycarbonyl-5,6,7,8-tetrahydro-5,5,8,8-tetramethyl-2-1H-benz[f]indolyl) benzoic acid which melts at 145-146° C. are obtained.

(h) p-(5,6,7,8-tetrahydro-5,5,8,8-tetramethyl-2-1H-benz[f]indolyl) benzoic acid 6.4 g (14 mmoles) of the ester obtained in 5(g) are treated at reflux for 4 hours with 100 ml of 2N methanolic soda. The solvent is evaporated and the remainder is taken up in water, acidifying the aqueous phase to pH 5 with HCl and extracted with ethyl ether. The organic phase is decanted, dried on $MgSO_4$ and evaporated. The residue is triturated in 100 ml of hexane. 4.3 g (40%) of p-(5,6,7,8-tetrahydro-5,5,8,8-tetramethyl-2-1H-benz[f]indolyl) benzoic acid which melts at 294-296° C. are obtained.

EXAMPLE 6

Preparation of the methyl ester of p-(5,6,7,8-tetrahydro-5,5,8,8-tetramethyl-2-1H-benz[f]indolyl) benzoic acid 2.3 g (6.6 mmoles) of p-(5,6,7,8-tetrahydro-5,5,8,8-tetramethyl-2-1H-benz[f]indolyl) benzoic acid are introduced into a round bottom flask containing 150 ml of methanol. There are slowly added 2 ml of concentrated sulfuric acid and the reaction mixture is heated at reflux for 4 hours. The reaction mixture is then evaporated to dryness and the remainder is taken up in water, alkalinized with sodium bicarbonate and extracted with methylene chloride. The organic phase is decanted, dried on $MgSO_4$ and evaporated. 2.3 g (96%) of the methyl ester of p-(5,6,7,8-tetrahydro-5,5,8,8-tetramethyl-2-1H-benz[f]indolyl) benzoic acid which melts at 212-213° C. are obtained.

EXAMPLE 7

Preparation of the methyl ester of p-(1-methyl-5,6,7,8-tetrahydro-5,5,8,8-tetramethyl-2-benz[f]indolyl) benzoic acid 180mg (5.1 mmoles) of sodium hydride (80% in oil) are suspended in 20 ml of DMF. There are slowly added 1.8 g (5 mmoles) of the ester prepared in Example 6, dissolved in 5 ml of THF. The reaction mixture is stirred until the evolution of gas ceases. There are then added 0.4 ml (6.4 mmoles) of methyl iodide and the reaction mixture is stirred for 2 hours at ambient temperature. The reaction mixture is poured into water and extracted with $CH_2Cl_2$. The organic phase is decanted, dried on $MgSO_4$ and evaporated. The residue is purified by chromatography on a silica column by eluting with a 4/1 mixture of dichloromethane and hexane. After evaporation of the solvents, 1.4 g (78%) of the methyl ester of p-(1-methyl-5,6,7,8-tetrahydro-5,5,8,8-tetramethyl-2-benz[f]indolyl) benzoic acid which melts at 147-148° C. are obtained.

EXAMPLE 8

Preparation of p-(1-methyl-5,6,7,8-tetrahydro-5,5,8,8-tetramethyl-2-benz[f]indolyl) benzoic acid 1.2 g (3.2 mmoles) of the ester obtained in Example 7 are treated at reflux for 2 hours with 100 ml of 2N methanolic soda. The mixture is heated for 2 hours at reflux, evaporated to dryness, taken up in water, the aqueous phase is acidified to pH 5 with HCl and extracted with ether. The organic phase is decanted, dried on MgSO₄ and evaporated. The residue is pulverized in 100 ml of hexane and then filtered to give 1.13 g (97%) of p-(1-methyl-5,6,7,8-tetrahydro-5,5,8,8-tetramethyl-2-benz[f]indolyl) benzoic acid which melts at 288-289° C.

EXAMPLE 9

Preparation of the methyl ester of p-(5,6,7,8-tetrahydro-5,5,8,8-tetramethyl-2-naphth[2,3-d]oxazolyl) benzoic acid (a) 5,6,7,8-tetrahydro-5,5,8,8-tetramethyl-2-naphthol.

54.9 g (300 mmoles) of 2,5-dichloro-2,5-dimethyl hexane are dissolved in dichloromethane (500 ml). There is then added phenol (28.2 g - 300 mmoles) and then aluminum chloride (8.0 g - 60 mmoles). The mixture is vigorously stirred for 16 hours. Water is then added (200 ml) and the mixture is extracted with dichloromethane (3×200 ml). The organic phase is washed with a saturated solution of sodium bicarbonate and then with a saturated solution of sodium chloride. It is then dried on magnesium sulfate, filtered and the solvents are evaporated.

The resulting solid is washed with a mixture composed of 80% hexane and 20% dichloromethane, (200 ml), yielding 5,6,7,8-tetrahydro-5,5,8,8-tetramethyl-2-naphthol: 43.5 g (71%), which melts at 142° C.

(b) 3-nitro-5,6,7,8-tetrahydro-5,5,8,8-tetramethyl-2-naphthol 5,6,7,8-tetrahydro-5,5,8,8-tetramethyl-2-naphthol (42.86 g - 210 mmoles) is dissolved in acetic anhydride (420 ml).

The solution is cooled to −10° C. and 40 ml of acetic acid are added. There is then added fuming nitric acid (8.7 ml - 210 mmoles) in solution in a mixture of acetic anhydride (40 ml) and acetic acid (40 ml). The reaction mixture is stirred for one hour at ambient temperature.

The reaction mixture is then poured into water (1 liter) plus ice. The precipitate that forms is filtered, washed with water, taken up in dichloromethane (3×200 ml). The organic phase is washed with a saturated solution of sodium bicarbonate and then with water. It is dried on magnesium sulfate, filtered and the solvent evaporated.

The resulting solid is purified by chromatography on silica and eluted with a 50/50 mixture of dichloromethane and hexane.

19.6 g (37%) of 3-nitro-5,6,7,8-tetrahydro-5,5,8,8-tetramethyl-2-naphthol which melts at 139° C. are obtained.

(c) 3-amino-5,6,7,8-tetrahydro-5,5,8,8-tetramethyl-2-naphthol.

3-nitro-5,6,7,8-tetrahydro-5,5,8,8-tetramethyl-2-naphthol (35.3 g - 14 mmoles) is mixed with methanol (1 liter).

To this mixture there are added about 2 spatulas full of Raney nickel washed with methanol and the mixture is hydrogenated until the end of absorption.

The precipitate that forms is dissolved by the addition of dichloromethane (1 liter).

The catalyst is filtered and the solvents are evaporated.

The resulting crystals are washed with hexane (2 liters) and then filtered. 30.9 g (99%) of 3-amino-5,6,7,8-tetrahydro-5,5,8,8-tetramethyl-2-naphthol which melts at 225° C. are obtained.

(d) Methyl ester of p-[(3-hydroxy-5,6,7,8-tetrahydro-5,5,8,8-tetramethyl-2-naphthyl)carbamoyl] benzoic acid 17.5 g (80 mmoles) of 3-amino-5,6,7,8-tetrahydro-5,5,8,8-tetramethyl-2-naphthol are mixed with ethyl ether (400 ml). Triethylamine (11.1 ml - 80 mmoles) is added and then slowly 15.81 g (80 mmoles) of p-methoxy carbonyl benzoyl chloride in solution in ether (200 ml).

The reaction mixture is stirred for 2 hours at ambient temperature and then poured into a mixture of water (500 ml) and dichloromethane (300 ml).

The aqueous phase is extracted with dichloromethane (2×300 ml) and the organic phase is washed with a saturated solution of sodium chloride, dried on magnesium sulfate, filtered and the solvent evaporated.

The resulting solid is purified by column chromatography and eluted with dichloromethane.

24.38 g (80%) of the methyl ester of p-[(3-hydroxy-5,6,7,8-tetrahydro-5,5,8,8-tetramethyl-2-naphthyl)carbamoyl]benzoic acid which melts at 200-210° C. are obtained.

(e) methyl ester of p-(5,6,7,8-tetrahydro-5,5,8,8-tetramethyl-2-naphth[2,3-d]oxazolyl) benzoic acid The methyl ester of p-[(3-hydroxy-5,6,7,8-tetrahydro-5,5,8,8-tetramethyl-2-naphthyl) carbamoyl] benzoic acid (23.25 g - 61 mmoles) is mixed with xylene (600 ml). There are added 11.6 g (61 mmoles) of p-toluene sulfonic acid and the mixture is heated at reflux, with stirring, for 3 hours. The xylene is evaporated and there are added water (500 ml) and some dichloromethane. There are then added to the aqueous phase about 300 ml of a saturated solution of sodium bicarbonate and the mixture is extracted with dichloromethane (3×300 ml). The organic phase is then washed with a saturated solution of sodium bicarbonate and then with water.

The organic phase is dried on magnesium sulfate, filtered and the solvents are evaporated.

The resulting solid is purified by column chromatography and eluted with a mixture of 80% dichloromehtane and 20% hexane.

The methyl ester of p-(5,6,7,8-tetrahydro-5,5,8,8-tetramethyl-2-naphth[2,3-d]oxazolyl) benzoic acid (12.25 g - 54%) which melts at 174° C. is obtained.

EXAMPLE 10

Preparation of p-(5,6,7,8-tetrahydro-5,5,8,8-tetramethyl-2-naphth[2,3-d]oxazolyl) benzoic acid The methyl ester of p-(5,6,7,8-tetrahydro-5,5,8,8-tetramethyl-2-naphth[2,3-d]oxazolyl) benzoic acid (7.27 g - 20 mmoles) is mixed with methanol (400 ml). There is then added 5N soda (40 ml) and the mixture is heated at reflux for 1 hour.

The methanol is evaporated and ethyl ether (300 ml) and 4N HCl (200 ml) are added. The aqueous phase is extracted with ether (2×300 ml) and the organic phase is washed twice with water and once with a saturated solution of sodium chloride.

The organic phase is dried on magnesium sulfate, filtered and the solvent evaporated.

The resulting solid is taken up in hexane (300 ml), filtered and dried. 7.00 g (100%) of p-(5,6,7,8-tetrahydro-5,5,8,8-tetramethyl-2-naphtho [2,3-d]oxazolyl) benzoic acid which melts at 290° C. are obtained.

EXAMPLE 11

Preparation of p-(5,6,7,8-tetrahydro-5,5,8,8-tetramethyl-2-naphth[2,3-d]oxazolyl) benzyl alcohol The methyl ester of p-(5,6,7,8-tetrahydro-5,5,8,8-tetramethyl-2-naphth[2,3-d]oxazolyl) benzoic acid (2.64 g - 7.26 mmoles) is dissolved in dry tetrahydrofuran (50 ml). This solution is slowly (474 mg - 11.9 mmoles) in suspension in dry tetrahydrofuran (50 ml).

The reaction mixture is heated at reflux for 5 hours, cooled to 0° C., then hydrolyzed by the slow addition of 30 ml of a solution of the double tartrate of sodium and potassium.

The solvent is evaporated, 300 ml of water are added and the product is extracted with ether (6×200 ml). The organic phase is washed with a saturated solution of sodium chloride and then dried on magnesium sulfate. After evaporation of the solvent, the product is recrystallized in acetonitrile. 216 g (89%) of p-(5,6,7,8-tetrahydro-5,5,8,8-tetramethyl-2-naphth[2,3-d]oxazolyl) benzyl alcohol which melts at 200° C. are obtained.

EXAMPLE 12

Preparation of p-(5,6,7,8-tetrahydro-5,5,8,8-tetramethyl-2-naphth[2,3-d]oxazolyl) benzoic aldehyde p-(5,6,7,8-tetrahydro-5,5,8,8-tetramethyl-2-naphth[2,3-d]oxazolyl) benzyl alcohol (1.24 g - 3.7 mmoles) is dissolved in dichloromethane (30 ml). There is then added pyridinium chlorochromate (1.20 g - 5.54 mmoles) in solution in 8 ml of dichloromethane. The reaction mixture is stirred for 2 hours at ambient temperature and the solvent is then evaporated.

The product is purified by column chromatography and eluted with a mixture composed of 80% ether and 20% hexane. The solvents are evaporated and the resulting solid is taken up in hexane, filtered and dried. 920 mg (75%) of p-(5,6,7,8-tetrahydro-5,5,8,8-tetramethyl-2 -naphth[2,3-d]oxazolyl) benzoic aldehyde which melts at 179° C. are obtained.

EXAMPLE 13

Preparation of the ethylamide of p-(5,6,7,8-tetrahydro-5,5,8,8-tetramethyl-2-naphth[2,3-d]oxazolyl) benzoic acid (a)

p-(5,6,7,8-tetrahydro-5,5,8,8-tetramethyl-2-naphth[2,3-d]oxazolyl) benzoic acid chloride p-(5,6,7,8-tetrahydro-5,5,8,8-tetramethyl-2-naphth[2,3-d]oxazolyl) benzoic acid (4.57 g - 13.1 mmoles) is suspended in dichloromethane (200 ml). There is then slowly added dicyclohexylamine (2.37 g - 13.1 mmoles) and the dichloromethane is then evaporated.

The resulting solid is taken up in ether (500 ml), filtered and then dried, yielding the dicyclohexylamine salt o p-(5,6,7,8-tetrahydro-5,5,8,8-tetramethyl-2-naphth[2,3-d]oxazolyl) benzoic acid (6.94 g - 100%).

The above salt is dissolved in dichloromethane (100 ml). The resulting solution is cooled to 0° C. and there is then slowly added thionylchloride (1.55 g - 13.1 mmoles).

The reaction mixture is stirred for 2 hours at ambient temperature. The formed dicyclohexylamine hydrochloride is filtered and the dichloromethane is evaporated.

The resulting crude acid chloride is used as such for the following synthesis.

(b) ethylamide of p-(5,6,7,8-tetrahydro-5,5,8,8-tetramethyl-2-naphth[2,3-d]oxazolyl) benzoic acid Ethylamine (216mg - 4.8 mmoles) is dissolved in dry tetrahydrofuran (25 ml). There are added successively triethylamine (485mg - 4.8 mmoles) and then slowly the acid chloride obtained in Example 13(a) (1.6 g - 4.4 mmoles) in solution in dry tetrahydrofuran (25 ml).

The reaction mixture is stirred for 1 hour at ambient temperature and then poured into 2N HCl (200 ml). The product is extracted with ether (3×100 ml), and then the organic phase is washed with water (3 times), then by a saturated solution of sodium chloride and dried on magnesium sulfate The solution is filtered and the solvents are evaporated The resulting solid is taken up in hexane (300 ml), filtered and dried. The ethylamide of p-(5,6,7,8-tetrahydro-5,5,8,8-tetramethyl-2-naphth[2,3-d]oxazolyl) benzoic acid (1.07 g - 65%) which melts at 174° C. is obtained.

EXAMPLE 14

Preparation of the morpholide of p-(5,6,7,8-tetrahydro-5,5,8,8-tetramethyl-2-naphth[2,3,-d]oxazolyl) benzoic acid Morpholine (417mg - 4 8 mmoles) is dissolved in dry tetrahydrofuran (25 ml) There are successively added triethylamine (485mg - 4.8 mmoles) and then slowly p-(5,6,7,8-tetrahydro-5,5,8,8-tetramethyl-2-naphth[2,3-d]oxazolyl) benzoic acid chloride (1.6 g - 4.4 mmoles) in solution in dry tetrahydrofuran (25 ml).

The reaction mixture is stirred for 2 hours at ambient temperature and then poured into 4N HCl (200 ml).

The product is extracted with ether (3×200 ml), the organic phase is washed with water (3 times) and then with a saturated solution of sodium chloride and finally dried on magnesium sulfate.

The solution is filtered and the solvents evaporated. The product is purified by chromatography on silica, eluted with a mixture of 50% dichloromethane, 20% ether and 30% hexane.

The solvents are evaporated and the resulting solid is taken up in hexane (300 ml).

The morpholide of p-(5,6,7,8-tetrahydro-5,5,8,8-tetramethyl-2-naphth[2,3-d]oxazolyl) benzoic acid (1.13 g - 62%) which melts at 193° C. is obtained.

EXAMPLE 15

Preparation of the 2-hydroxyethyl ester of p-(5,6,7,8-tetrahydro-5,5,8,8-tetramethyl-2-naphth[2,3-d]oxazolyl) benzoic acid Ethylene glycol (298mg - 4.8 mmoles) is dissolved in dry dichloromethane (25 ml). There are successively added pyridine (380mg - 4.8 mmoles) and then slowly p-(5,6,7,8-tetrahydro-5,5,8,8-tetramethyl-2-naphth[2,3-d]oxazolyl) benzoic acid chloride (1.6 g - 4.4 mmoles) in solution in dry dichloromethane (25 ml).

The reaction mixture is stirred for 2 hours at ambient temperature and then poured into 200 ml of 4N HCl.

The product is extracted with ether (3×200 ml). The organic phase is washed with water (3 times) and then with a saturated solution of sodium chloride and finally dried on magnesium sulfate.

The solution is filtered and the solvents are evaporated. The product is purified by chromatography on silica, eluted by a mixture of 70% dichloromethane and 30% ether.

875mg (51%) of the 2-hydroxyethyl ester of p-(5,6,7,8-tetrahydro-5,5,8,8-tetramethyl-2-naphth [2,3-d]oxazolyl) benzoic acid which melts at 144° C. are obtained.

EXAMPLE 16

Preparation of the methyl ester of p-(5,6,7,8-tetrahydro-5,5,8,8-tetramethyl-2-naphth[2,3-d]imidazolyl) benzoic acid (a) 2,3-dinitro-5,6,7,8-tetrahydro-5,5,8,8-tetramethyl naphthalene 91.5 g (490 mmoles) of 5,6,7,8-tetrahydro-5,5,8,8-tetramethyl naphthalene are dissolved in concentrated sulfuric acid (365 ml). The solution is cooled to 0° C. and there is added, with mechanical stirring, fuming nitric acid (365 ml).

The reaction mixture is stirred for 2 hours at ambient temperature and then poured over ice.

The product is extracted with ethyl ether (3×1 liter). The organic phase is neutralized by the addition of solid sodium bicarbonate (+300 ml of water), decanted and dried on magnesium sulfate.

The organic phase is filtered, the solvent is evaporated and the resulting solid is recrystallized in cyclohexane.

80.19 g (59%) of 2,3-dinitro-5,6,7,8-tetrahydro-5,5,8,8-tetramethyl naphthalene, which melts at 200° C. are obtained.

(b) 2,3-diamino-5,6,7,8-tetrahydro-5,5,8,8-tetramethyl naphthalene 36.12 g (130 mmoles) of 2,3-dinitro-5,6,7,8-tetrahydro-5,5,8,8-tetramethyl naphthalene are dissolved in 1 liter of methanol. There are added about 2 spatulas-full of Raney nickel and the mixture is washed with methanol and hydrogenated until the end of absorption The catalyst is filtered, the solvents are evaporated and the resulting solid is washed with about 300 ml of hexane.

14.49 g (51%) of 2,3-diamino-5,6,7,8-tetrahydro-5,5,8,8-tetramethyl naphthalene which melts at 185° C. are obtained.

(c) methyl ester of p-[(3-amino-5,6,7,8-tetrahydro-5,5,8,8-tetramethyl-2-naphthyl)carbamoyl] benzoic acid 2,3-diamino-5,6,7,8-tetrahydro-5,5,8,8-tetramethyl naphthalene (6.55 g - 30 mmoles) is mixed with methyl ether (170 ml); there are added to the mixture triethylamine (4.2 m-30 mmoles) and then, slowly, methyl p-chloroformyl benzoate (5.96 g - 30 mmoles) in solution in ether (70 ml).

The reaction mixture is stirred for 2 hours at ambient temperature and it is then poured into a mixture of water (400 ml) and dichloromethane (400 ml).

The organic phase is washed with a saturated solution of sodium bicarbonate, then with a saturated solution of sodium chloride, dried on magnesium sulfate, filtered and the solvents evaporated.

The resulting solid is purified by column chromatography, eluted with a system composed of 10% ethyl ether and 90% dichloromethane.

3.73 g of the methyl ester of p-[3-amino-5,6,7,8-tetrahydro-5,5,8,8-tetramethyl-2-naphthyl) carbamoyl] benzoic acid in the form of a white solid are obtained.

(d) methyl ester of p-(5,6,7,8-tetrahydro-5,5,8,8-tetramethyl-2-naphth[2,3-d] imidazolyl benzoic acid 3.65 g (9.6 mmoles of the methyl ester p-[(3-amino-5,6,7,8-tetrahydro-5,5,8,8-tetramethyl-2-naphthyl)carbamoyl] benzoic acid are dissolved in xylene (200 ml) To the solution there is added p-toluene sulfonic acid monohydrate (1.82 g - 9.6 mmoles) and the mixture is heated at reflux, with stirring, for 1 hour. The xylene is evaporated and there are added 300 ml of water and 300 ml of a saturated solution of sodium bicarbonate. The aqueous phase is extracted with dichloromethane (3×300 ml) and the organic phase is washed with a saturated solution of sodium chloride, dried on magnesium sulfate, filtered and the solvents evaporated. The resulting solid is purified by column chromatography and eluted with a mixture composed of 95% dichloromethane and 5% ethyl ether 2.7 g (78%) of the methyl ester of p-(5,6,7,8-tetrahydro-5,5,8,8-tetramethyl-2-naphth [2,3-d]imidazolyl) benzoic acid which melts at 270–275° C. (decomposition) are obtained.

EXAMPLE 17

Preparation of p-(5,6,7,8-tetrahydro-5,5,8,8-tetramethyl-2-naphth[2,3-d]imidazolyl) benzoic acid 1.52 g (4.2 mmoles) of the methyl ester of p-(5,6,7,8-tetrahydro-5,5,8,8-tetramethyl-2-naphth [2,3-d]imidazolyl) benzoic acid are mixed with 300 ml of methanol. There is added to the mixture 5N soda solution (8.4 ml) and it is heated at reflux for 24 hours.

The methanol is evaporated and the pH is then adjusted to 5 by the addition of 1N HCl.

The product is extracted with ether (5×400 ml), and the organic phase is washed with water (2×500 ml) and then with a saturated solution of sodium chloride (2×300 ml).

The organic phase is dried on magnesium sulfate, filtered and the solvents are evaporated. The resulting solid is taken up in 300 ml of hexane, filtered and oven dried.

920mg (63%) of p-(5,6,7,8-tetrahydro-5,5,8,8-tetramethyl-2-naphth[2,3-d]imidazolyl) benzoic acid, which melts at 250° C. (decomposition), are obtained.

EXAMPLE 18

Preparation of 2-(4-methyl)phenyl-5,6,7,8-tetrahydro-5,5,8,8-tetramethyl naphth[2,3-d]imidazole (a) N-(3-amino-5,6,7,8-tetrahydro-5,5,8,8-tetramethyl-2-naphthyl)-4-methylbenzamide 4 g (18 mmoles) of 2,3-diamino-5,6,7,8-tetrahydro-5,5,8,8-tetramethyl naphthalene are suspended in 100 ml of ether. There are added to the suspension triethylamine (2.55 ml - 18.3 mmoles) and then 2.83 g (18.3 mmoles) of 4-methyl benzoyl chloride in solution in 50 ml of ether.

The reaction mixture is stirred for 1 hour and there are then added 300 ml of dichloromethane. The aqueous phase is extracted with dichloromethane (2×300 ml) and the organic phase is washed with a saturated solution of sodium chloride The organic phase is dried on magnesium sulfate, filtered and the solvents are evaporated.

The product is purified by column chromatography and eluted with a mixture of 10% ether and 90% dichloromethane.

2.75 g (45%) of N-(3-amino-5,6,7,8-tetrahydro-5,5,8,8-tetramethyl-2-naphthyl)-4-methylbenzamide, which melts at 180° C. are obtained.

(b) 2-(4-methyl)phenyl-5,6,7,8-tetrahydro-5,5,8,8-tetramethyl-naphth-[2,3-d]imidazole 2.72 g (8.1 mmoles) of N-(3-amino-5,6,7,8-tetrahydro-5,5,8,8-tetramethyl naphthyl)-4methylbenzamide are mixed with 150 ml of xylene. There are added to the mixture 1.54 g (8.1 mmoles) of p-toluene sulfonic acid and the mixture is heated at reflux for 2 hours. The xylene is evaporated and there are added 300 ml of water and 300 ml of dichloromethane.

The aqueous phase is extracted with dichlormethane. The organic phase is washed with a saturated solution of sodium chloride, dried on magnesium sulfate, filtered and the solvents are evaporated.

The product is purified by column chromatography and eluted with a mixture of 10% ether and 90% hexane.

1.78 g (69%) of 2-(4-methyl)phenyl-5,6,7,8-tetrahydro-5,5,8,8-tetramethyl-naphth[2,3-d]imidazole are obtained.

EXAMPLES OF COMPOSITIONS

A. Oral Compositions

| Example I - 0.2 g tablet | |
|---|---|
| p-(5,6,7,8-tetrahydro-5,5,8,8-tetramethyl-2-naphtho [2,3-b] thienyl) benzoic acid | 0.0001 g |
| Dicalcium phosphate | 0.020 g |
| Silica | 0.020 g |
| Lactose | 0.030 g |
| Talc | 0.010 g |
| Magnesium stearate | 0.005 g |
| Starch, sufficient amount for | 0.200 g |

In this Example, the active compound can be replaced by its methyl ester.

| Example II - 0.4 g capsule | |
|---|---|
| p-(5,6,7,8-tetrahydro-5,5,8,8-tetramethyl-naphtho[2,3-b] furan-2-yl benzoic acid | 0.0002 g |
| Glycerine | 0.200 g |
| Sucrose | 0.050 g |
| Polyethylene glycol 400 | 0.050 g |
| Purified water, sufficient amount for | 0.400 g |

The capsule is made of gelatin, glycerine, titanium dioxide and water.

| Example III - 0.5 g gelule | |
|---|---|
| Morpholide of p-(5,6,7,8-tetrahydro-5,5,8,8-tetramethyl-2-naphth[2,3-d]oxazolyl) benzoic acid | 0.0005 g |
| Cornstarch | 0.150 g |
| Magnesium stearate | 0.250 g |
| Sucrose, sufficient amount for | 0.500 g |

The above powder is packaged in a gelule composed of gelatin and TiO₂.

B. Topical Compositions

| Example IV - Ointment | |
|---|---|
| p-(5,6,7,8-tetrahydro-5,5,8,8-tetramethyl-2-naphth[2,3-d]oxazolyl) benzoic acid | 0.0001 g |
| Stearyl alcohol | 3.000 g |
| Lanolin | 5.000 g |
| Petrolatum | 15.000 g |
| Distilled water, sufficient amount for | 100.000 g |

| Example V - Ointment | |
|---|---|
| p-(5,6,7,8-tetrahydro-5,5,8,8-tetramethyl-2-1H-benz[f]indolyl) benzoic acid | 0.0005 g |
| Stearyl alcohol | 3.000 g |
| Lanolin | 5.000 g |
| Petrolatum | 15.000 g |
| Distilled water, sufficient amount for | 100.000 g |

| Example VI - Gel | |
|---|---|
| Methyl ester of p-(5,6,7,8-tetrahydro-5,5,8,8-tetramethyl-2-naphtho[2,3-b]furan-2-yl) benzoic acid | 0.0005 g |
| Hydroxypropyl cellulose, sold by Hercules under the trade name "Klucel HF" | 2.000 g |
| Water/ethanol, 50:50, sufficient amount for | 100.000 g |

What is claimed is:

1. A polycyclic heterocyclic compound having the formula

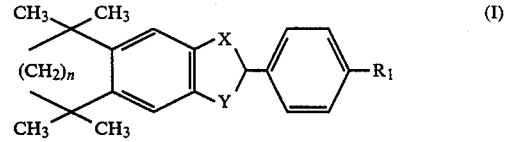

(I)

wherein
n is 1 or 2,
R₁ represents (i) hydrogen, (ii) —CH₂OH or (iii)

R₂ represents (a) hydrogen, (b)

or (c) —OR₃ wherein R₃ represents hydrogen, alkyl having 1–20 carbon atoms, monohydroxyalkyl, polyhydroxyalkyl, phenyl, phenyl substituted by halogen, hydroxy, nitro or lower alkyl, benzyl, phenethyl, a sugar radical selected from the group consisting of glucose, mannose, erythrose and galactose, or

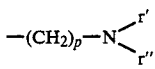

wherein p is 1, 2 or 3 and r' and r" represents hydrogen, lower alkyl, monohydroxyalkyl, polyhydroxyalkyl, phenyl, phenyl substituted by halogen, hydroxy, nitro or lower alkyl, aminated sugar radical selected from the group consisting of glucosamine, galactosamine and mannosamine, or r' and r" taken together form a heterocycle selected from the group consisting of piperidino, piperazino, morpholino, pyrrolidino and 4-(2'-hydroxyethyl) piperazino, X represents oxygen, Y represents a nitrogen atom, or a salt of said polycyclic heterocyclic compound of formula I.

2. A polycyclic heterocyclic compound having the formula

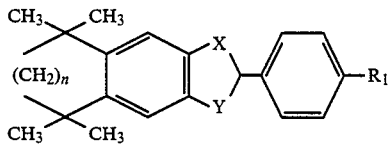

wherein
n is 1 or 2,
R₁ represents (i) hydrogen, (ii) —CH₂OH or (iii)

R₂ represents (a) hydrogen, (b)

or (c) —OR₃ wherein R₃ represents hydrogen, alkyl having 1–20 carbon atoms, monohydroxyalkyl, polyhydroxyalkyl, phenyl, phenyl substituted by halogen, hydroxy, nitro or lower alkyl, benzyl, phenethyl, or

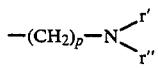

wherein p is 1, 2 or 3 and r' and r" represent hydrogen, lower alkyl, monohydroxyalkyl, polyhydroxyalkyl, phenyl, phenyl substituted by halogen, hydroxy, nitro or lower alkyl, or r' and r" taken together form a heterocycle selected from the group consisting of piperidino, piperazino, morpholino, pyrrolidino and 4-(2'-hydroxyethyl) piperazino, X represents oxygen, Y represents a nitrogen atom, or a salt of said polycyclic heterocyclic compound of formula I.

3. The compound of claim 1 wherein said lower alkyl has 1–4 carbon atoms.

4. The compound of claim 2 wherein said lower alkyl is methyl, ethyl, isopropyl, butyl or tert.butyl.

5. The compound of claim 1 wherein said monohydroxyalkyl has 2–4 carbon atoms.

6. The compound of claim 4 wherein said monohydroxyalkyl is 2-hydroxyethyl, 2-hydroxypropyl or 2'-hydroxy-2-ethoxyethyl.

7. The compound of claim 1 wherein said polyhydroxyalkyl has 3–6 carbon atoms and 2–5 hydroxyl groups.

8. The compound of claim 6 wherein said polyhydroxyalkyl is 2,3-dihydroxypropyl, 2,3,4-trihydroxybutyl,2,3,4,5-tetrahydroxypentyl or the residue of pentacrythritol.

9. The compound of claim 1 having the formula

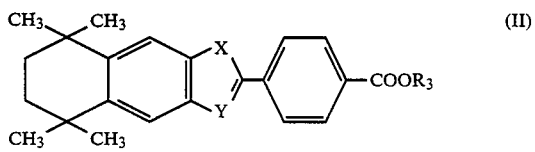

wherein
R₃ represents hydrogen or lower alkyl,
X represents oxygen,
Y represents a nitrogen atom,
R₄ represents hydrogen or methyl.

10. The compound of claim 2 selected from the group consisting of
methyl ester of p-(5,6,7,8-tetrahydro-5,5,8,8-tetramethyl-2-naphth [2,3-d] oxazolyl) benzoic acid,
p-(5,6,7,8-tetrahydro-5,5,8,8-tetramethyl-2-naphth [2,3-d]oxazolyl) benzoic acid,
p-(5,6,7,8-tetrahydro-5,5,8,8-tetramethyl-2-naphth [2,3-d]oxazolyl) benzyl alcohol,
p-(5,6,7,8-tetrahydro-5,5,8,8-tetramethyl-2-naphth [2,3-d]oxazolyl) benzoic aldehyde,
ethylamide of p-(5,6,7,8-tetrahydro-5,5,8,8-tetramethyl-2-naphth [2,3-d] oxazolyl) benzoic acid,
morpholide of p-(5,6,7,8-tetrahydro-5,5,8,8-tetramethyl-2-naphth [2,3-d]oxazolyl) benzoic acid, and
2-hydroxyethyl ester of p-(5,6,7,8-tetrahydro-5,5,8,8-tetramethyl-2-naphth [2,3-d] oxazolyl) benzoic acid.

11. A pharmaceutical composition for the treatment of a dermotologic, rheumatoidal, respiratory or opthalmologic disorder containing in a vehicle suitable for enteral, parenteral, rectal, topical or ocular administration an effective amount of a compound of formula I of claim 1.

12. The pharmaceutical composition of claim 11 in a vehicle for topical application, said composition containing said compound to 0.01 percent by weight based on the total weight of said composition.

* * * * *